United States Patent [19]
Nagasampagi et al.

[11] Patent Number: 5,663,374
[45] Date of Patent: Sep. 2, 1997

[54] TRITERPENE DERIVATIVES OF AZADIRACHTIN HAVING INSECT ANTIFEEDANT AND GROWTH INHIBITORY ACTIVITY AND A PROCESS FOR EXTRACTING SUCH COMPOUNDS FROM THE NEEM PLANT

[75] Inventors: Bhimsen Annacharya Nagasampagi; Supada Rambhau Rojatkar; Mandakini Moreshwar Kulkarni; Vimal Shantaram Joshi; Vidya Sudhir Bhat; Mukund Gangadhar Sane; Nagaraj Ramanuj Ayyangar, all of Maharashtra, India

[73] Assignee: Council of Scientific & Industrial Research, New Delhi, India

[21] Appl. No.: 585,239

[22] Filed: Jan. 11, 1996

Related U.S. Application Data

[62] Division of Ser. No. 319,298, Oct. 6, 1994, Pat. No. 5,602, 261, which is a division of Ser. No. 977,618, Nov. 17, 1992, Pat. No. 5,395,951.

[51] Int. Cl.$^6$ .................... A01N 43/16; A01N 31/02; C07C 57/02
[52] U.S. Cl. .................. 549/381; 549/383; 514/453; 554/8; 554/12; 554/13; 554/14
[58] Field of Search ................... 549/383, 381; 514/453, 783; 554/8, 12, 13, 14

[56] References Cited

U.S. PATENT DOCUMENTS 4,902,713  2/1990  Rembold ..................... 549/388

Primary Examiner—Nicky Chan
Attorney, Agent, or Firm—Ladas & Parry

[57] ABSTRACT

The invention discloses novel triterpene derivatives of azadirachtin of the formulae 2 to 11 of the drawings and a process for isolating new triterpene derivatives of azadirachtin from the various parts of the neem plant(Azadirachta indica A-Juss), which process comprises grinding the parts of the neem plant to get a powder, extracting the powder with a binary immiscible solvent consisting of one polar and another non-polar solvent in a ratio of 1:2 to obtain an extract, filtering the extract to get a filtrate having two layers, one layer containing lipids and the other layer containing the new triterpene derivatives of azadirachtin and water soluble constituents including sugars, separating the layers by known methods, concentrating the layer containing the new triterpenes of the formulae 2–11 including derivatives of azadirachtin and water soluble salts, treating the resultant concentrate with a polar solvent and if necessary, warm the concentrate having the solvent, and filtering/decanting the resultant solution to produce a filtrate containing the mixture of the new triterpene derivatives of azadirachtin. The lipid layer is concentrated in any known manner, the lipid concentrate is treated with a polar solvent, chilled to a temperature of 0° to −10° C. and filtered to produce a filtrate containing lipids. The new triterpene derivatives of azadirachtin are useful in suppressing the insect pest population below the econcmic threshold level by their antifeedant and growth inhibitory activities.

15 Claims, 5 Drawing Sheets

(1)

ESTIMATION OF AZADIRACHTIN (S) IN TRITERPENE- ACTIVE FRACTION OF NEEM BY HPLC.

TRITERPENE DERIVATIVES OF AZADIRACHTIN HAVING INSECT ANTIFEEDANT AND GROWTH INHIBITORY ACTIVITY AND A PROCESS FOR EXTRACTING SUCH COMPOUNDS FROM THE NEEM PLANT

This is a divisional of application Ser. No. 08/319,298 filed Oct. 6, 1994, now U.S. Pat. No. 5,602,261 which is a divisional of application Ser. No. 07/977,618 filed Nov. 17, 1992, now U.S. Pat. No. 5,395,951.

The present invention relates to novel triterpene derivatives of azadirachtin from neem plant (Azadirachta indica A. Juss) and a process for preparing novel triterpene derivatives of azadirachtin. The new triterpene derivatives of azadirachtin so prepared are useful in suppressing the insect pest population below the economic threshold level by their antifeedant and growth inhibitory activities.

BACKGROUND OF THE INVENTION

1. Field of the Invention

The imbalance in the ecosystem, human health hazards and the development of resistance by some insect pests caused by the continuous use of conventional insecticides have necessitated the search for alternative safer pesticides. Botanicals by virtue of their relatively low toxicity, biodegradability and many other factors acceptable to the environment are considered as the best alternatives to toxic chemicals. Among Botanicals, neem tree ranks first in view of its excellent pest control properties, its low mammalian toxicity and relative abundance in countries like India, Pakistan, Burma, Sri Lanka and Africa. No other tree or plant possessing insect-control properties, has received as much attention as neem world over which is evident from the three International and one National (India) conferences held during the past decade.

2. Description of the Prior Art

Although the protection of stored food grains, woolen clothes, fruits and vegetables by neem leaves has been used in India since time immemorial, the first report of the pesticidal properties appeared around 1927 when Mann and Burns [Agri. J. India, Calcutta 22, 325 (1927)] observed during the locust cycle of 1926–27 that adult locusts did not feed on neem leaves. This was followed by Chopra [Rept. of Dept. of Agr., Punjab Pt.2, Vol. 1. P.67 (1928)] who treated the extract of neem leaves as contact poison on grub weevils. Since then a number of publications describing the various activities from different parts of neem tree have appeared. For example, neem oil has shown antifeedant activity against Nephotettix virescens (leaf hopper of rice). [Neem Newsletter 1 (3) 28 (1984)]. Neem seed extract has shown antifeedant activity against Mythimna separata (rice ear cutting caterpillar) [Neem Newsletter 1 (3), 31 (1984)]. Neem cake has exhibited antifeedant activity against Nilaparvat lugens (Rice Brown Plant Hopper) [J. Economic Entol., 77, 502 (1984)]. Neem oil has shown oviposition deterrent and ovicidal activity against a stored grain pest of rice Corcyra cephalonica (rice moth). Neem seed kernel water suspension has shown oviposition deterrent activity against Spodoptera litura (Tobacco caterpillar) [Phytoparasitica 7(3), 199 (1979)]. Neem leaves extract has shown antifeedant activity against Rhizopertha dominica (lesser grain borer) [Neem Newsletter, 1 (2), 20 (1984)]. Neem root exudates have been reported to contain allelochemicals.

The first active principle exhibiting antifeedant properties against locusts (Schistocerca gregaria) was isolated in 1968 which was named as azadirachtin by Morgan and Butterwoth [Chem. Commn. 23 (1968)]. Since then azadirachtin has been shown to exhibit insect antifeedant and/or growth-inhibitory activities on more than 50 insect species. For example it has exhibited antifeedant activity at a dosage of 0.005% on Earias fabia (spotted cotton ballworm, family, Lepidoptera) [Phytoparasitica, 9 (1), 27 (1981)]. It has shown growth inhibitory activity at a dosage of 5–10 ppm against Spodoptera litura (tobacco caterpillar, Lepidoptera [Proceedings of the National Seminar on Neem in Agri.,] IARI, New Delhi, (1983); Indian J. Expt. Biol, 23(3), 16 (1985) and $LD_{50}$ of azadirachtin against S. litura is reported to be 1.1 g/g [J. Entomol. Res., 11 (2), 166 (1987)]. It has been reported to exhibit sterilant, insecticidal, delay in egg hatching, growth inhibitory and antifeedant activities at a dosage of 10–100 ppm against Epilachna verivestis (Maxican bean beetle, Coleoptera [Z pflakrankh pflaschutz, 82 (3), 176 (1975); Z. Angew Entomol, 93, 12 (1982);

Systemic action of azadirachtin through roots to leaves has been reported by Saxena et al [J. Econ. Entomol., 77 (2) 502 (1984)].

The drawing accompanying this specification shows the structure of azadirachtin in formula 1 which was established in 1986 by three groups of workers [Tetrahedron, 43, 2789; 2805, 2817 (1987)].

Till this time more than 80 tetranortriterpenes and derivatives of azadiraachtin have been isolated from neem extracts. Some of them are mentioned here: -nimbinene, nimbandiol, azadiradione, salannin, vilasinin, gedunin, meldenindiol and nimbin. Out of them at least 35 tritenpene derivatives show either insect antifeedant activity growth-inhibitory activity or both. For example azadirachtin A, B, D, E, F and G show insect growth inhibitory activities against Epilachna verivestis at a dosage of 1–10 ppm [Insecticides of Plant Origin, ACS Symposium series, 387, 150 (1989)]. Similarly 3-tigloylazadirachtol has exhibited 97% antifeedant activity at a dosage of 1.0 ppm [Tetrahedron, 45, 5175 (1989)]. Amongst other compounds azadiradione, azadirone, 6-deacetylnimbinene, epoxyazadiradione, gedunin, nimbandiol, salannin and salannol have shown antifeedant and growth-inhibitory activity against E. Verivestis [Proceedings, 2nd International Neem Conference 181 (1983)]. Azadirachtin has been reported to be active against nematodes and whitegurbs [Entomol. Exp. Appl., 24, 448 (1978).

Synthetic insecticides belonging to the class of organochlorine and organophosphorous are found to be quite toxic to mammals, fish, honeybees etc. They pollute the ecosystem by their toxicity and residual action. In addition they cause serious health hazards to human beings. In view of this there is an urgent need to look for safer alternatives and plant products appear to be the right choice because of their relatively low toxicity and biodegradability.

With the above objective we have made extensive research on the pest control properties of the extract from neem seeds and have observed that if the undesirable components viz. the saturated fats and the water soluble compounds including sugars are removed, the resulting extract is enriched with the required active compounds viz, the triterpenoids and the unsaturated fats.

Neem seed extract contains essentially four components namely saturated and unsaturated fats, triterpenoids and water soluble compounds containing sugars. Of these, triterpenoids exhibit insect-antifeedant and growth-inhibitory activity while the unsaturated fats possess insecticidal activity against aphids, mites, jassids, cotton white flies and other soft bodied insects. Of the remaining two, saturated fats are inactive and phytotoxic (above 2% dosage) and the water soluble sugars act as insect attractants and fungal growth promoters. Both these are undesirable in the formulation of pest control agents from neem.

In the known processes of preparing insecticidal composition from neem no attempt has been made to separate all the above said four components so that the concentration of the required compounds, the triterpenoids and the unsaturated fats can be used advantageously for pest control purposes. Some of the processes involve expelling neem oil which contains a low percentage (0.05) of active triterpenoids and directly use for pest control purposes. In some other processes the neem is extracted using a solvent like (hexane) to obtain an oil containing low percentage (0.05) of the active triterpenoids. Consequently, due to the very low percentage of the terpenoids these oils used directly for pest control purposes do not have desirable pest control properties.

A mixture of neem oil, karanja oil, mohua oil, gingely oil, castor oil has also been used but it exhibits phytotoxic properties in field trials. Neem based fertilizer in which neem extractive (crude) is blended with urea and sold as a fertilizer is also commercially available.

In the process of the present invention we have removed all the drawbacks of the existing processes by complete extraction of neem seed powder and solvent partitioning in one step using two immiscible solvents, forming two layers, one solvent layer containing the lipids and the other solvent layer containing the triterpenes and water soluble compounds including sugars. The second solvent layer is treated with a polar solvent in which the triterpenes only are soluble, thus separating them from the undersired sugar fraction by filtration/decantation. Thus, in two steps the active rich triterpenoid fraction exhibiting insect antifeedant and growth-inhibitory activity is obtained which is free from the undesirable lipids and water soluble compounds including sugars. The percentage of the active triterpenoid fraction is about 2.5% based on the seed powder.

Similarly the separation of the undesirable saturated fat (9%) from the total lipids has been achieved by fractional crystallisation from acetone at 0°–10° C. The saturated fats, at the above temperature solidify and are removed by filtration and the unsaturated fats remain in the mother liquor.

During our continued research in the field of pest control agents we observed that 1) neem seed extract is more active biologically than the extract of any other part of the neem tree. 2) Neem seed extract is more active than neem seed kernel extract as the husk or hull of the seeds also contains active principles. 3) Neem seed extract is more active than the expelled oil. 4) Triterpene fraction of the seed extract exhibits antifeedant activity and insect-growth inhibiting activity, while the lipid fraction rich in unsaturated fats is responsible for aphidicidal, miticidal and insecticidal activity against sucking pests and soft bodied insects.

SUMMARY OF THE INVENTION

The present invention provides new triterpene derivatives of azadirchtin from the parts of neem plant (A indica). These new triterpenes have the formulas 2–11 shown in the drawings accompanying this specification.

Another object of the present invention is to provide a process for the preparation of the new triterpenes.

Yet another object of the present invention is to provide a process for the prepration of an extract containing these new triterpenes which are useful as insecticidal compositions.

Still another object of the present invention is to provide a process for the preparation of insecticidal compositions containing lipids.

Though any part of the neem plant can be used in carrying out the present invention disclosed herein, it is preferred to employ the seed or the neem cake powder due to the above findings, that neem seed extract and neem seed cake extract have excellent insect-control activity.

DETAILED DESCRIPTION OF THE INVENTION

Figure 1:
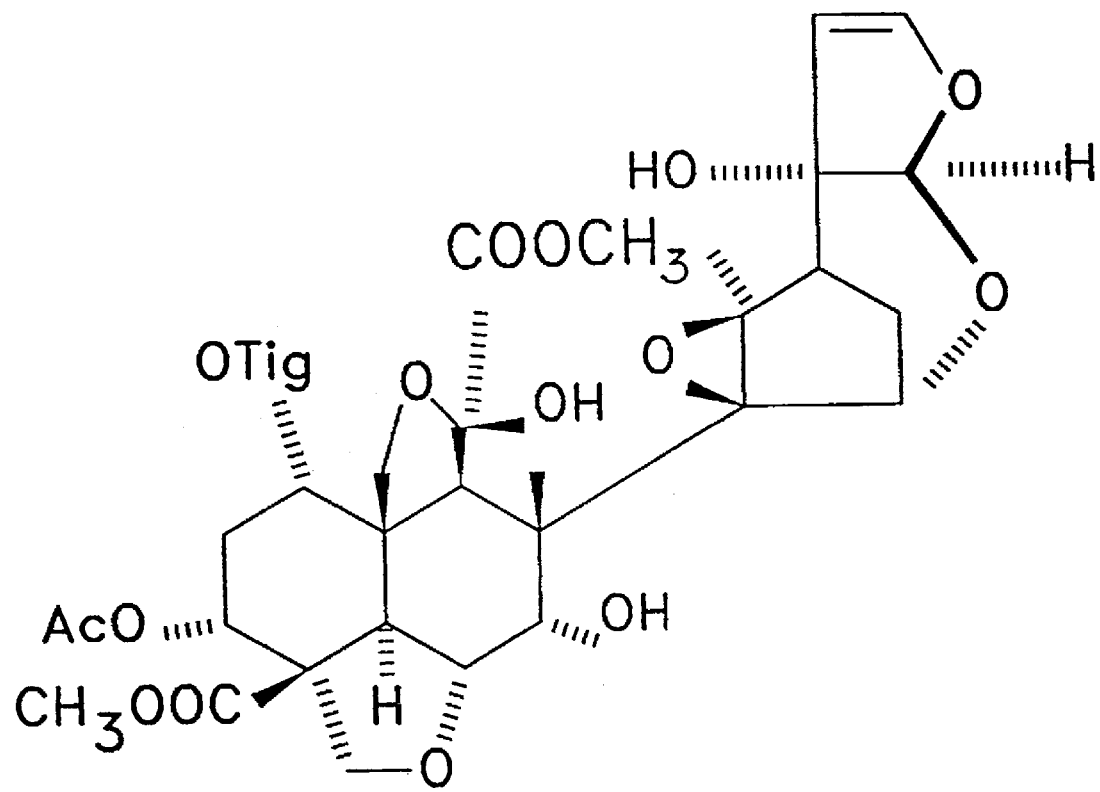
FIG. 1—shows the structure of azadirachtin.

Accordingly, present invention provides a process for the isolation of new triterpene derivatives of azadirachtin having the formulas 2–11 shown in the drawing accompanying the specification, from the parts of the neem plant, which comprises:

a. grinding the parts of the neem plant to get a powder;

b. extracting the powder with a binary immiscible solvent consisting of one polar and another non-polar solvent in the ratio of 1:2 to obtain an extract;

c. filtering the extract to obtain a filtrate having 2 layers, one layer containing lipids and another layer containing new triterpenes, azadirachtin and water soluble sugars;

d. separating the layers by known methods;

e. concentrating the polar solvent layer containing the new triterpene derivatives of azadirachtin and water soluble constituents;

f. treating the resultant concentrate with a polar solvent; and g. filtering/decanting the resultant solution to produce a filtrate containing the mixture of new triterpene derivatives of azadirachtin of the formulas 2–11 and known triterpenes including azadirachtin, separating the new triterpene derivatives of azadirachtin by column chromatography.

The separation of the new derivatives may be done using elutes such as ethyl acetate, benzene, acetone, and pet-ether. 120 g of triterpene-active fraction was subjected to column chromatography over Silica gel (60–120 mesh size, 2 kg) using acetone:pet-ether as the elution gradient to collect four broad fractions A (25 g), B (20 g), C (45 g) and D (20 g).

Fraction D (20 g) was put for further fractionation by column chromatography over Silica gel (60–120 mesh, 750 g) using chloroform:methylcyanide as the elution gradient to collect five broad fractions D1 (4 g), D2 (5 g), D3 (1.5 g), D4 (2 g), D5 (7 g) which contained mainly the azadirachtin and azadirachtin derivatives. Out of these, D1 and D2 fractions contained mainly salannin, salannol, nimbandiol and vilasinnin and its derivatives. D3 and D4 fractions contained azadirachtin and its derivatives and D5 fraction contained mostly polar compounds.

Azadirachtin and its new derivatives were isolated from D3 and D4 fractions by repeated column chromatography and preparative TLC using different solvent mixtures such as acetone:pet-ether (4:6), ethylacetate:benzene (9:1) and chloroform:methylcyanide (5:2). The Rf values of the ten new azadirachtin derivatives are different in each solvent system. But we could say that the compound No. (2), (4), (8), (9) and (10) are less polar than azadirachtin in all of the three above solvent systems and the remaining five compounds are more polar than azadirachtin. The structures of the above new azadiirachtin derivatives were established by spectral data (Chart 1 & 2).

$^1$H-NMR DATA OF COMPOUND 2–11 (CHART-1)

| Serial No. | 2 | 3 | 4 | 5 | 6 |
|---|---|---|---|---|---|
| 1-H | 3.58(m) | 4.68(dd) (2.75; 3.0) | 4.66(dd) (2.7; 3.1) | 3.40(m) | 5.34(dd) (2.65; 2.60) |
| 2-H | 2.3(ddd) (16.2; 2.65; 3.1) | 2.36(ddd) (16.3; 2.8; 3.2) | 2.34(ddd) (16.2; 2.8; 3.1) | 2.38(ddd) (16.3; 2.65; 3) | 2.32(ddd) (16.38; 3.48; 3.22) |
| 2-H | 2.12(ddd) (16.2; 2.95; 2.8) | 2.16(ddd) (16.3; 3.0; 2.8) | 2.20(ddd) (16.2; 3.0; 2.8) | 2.32(ddd) (16.3; 3.1; 2.65) | 2.29(ddd) (16.38; 3.22; 3.11) |
| 3-H | 5.45(t) (2.7; 3.1) | 4.48(t) (2.7; 2.8) | 5.44(t) (2.7; 2.9) | 5.48(t) (2.75; 2.8) | 5.50(t) (2.7; 3.08) |
| 5-H | 3.3(d) (12.5) | 3.09(d) (12.5) | 3.30(d) (12.5) | 3.24(d) (12.5) | 3.34(d) (12.5) |
| 6-H | 4.40(dd) (12.5; 2.7) | 4.15(dd) (12.5; 2.75) | 4.44(dd) (12.5; 2.8) | 4.48(dd) (12.5; 2.65) | 4.43(dd) (12.5; 3.73) |
| 7-H | 4.62(d) (2.7) | 4.65(d) (2.65) | 4.64(d) (2.65) | 4.8(d) (2.63) | 4.62(d) (2.2) |
| 9-H | 2.62(s) | 3.32(s) | 3.30(s) | 3.30(s) | 2.62(s) |
| 11-H | 4.50(s) | — | — | 4.53(s) | 5.38(s) |
| 15-H | 4.56(d) (3.20) | 4.58(d) (3.20) | 4.64(d) (3.20) | 4.50(d) (3.20) | 4.55(d) (3.20) |
| 16-H | 1.65(ddd) (13.0; 3.5; 5.3) | 160(ddd) (13.0; 3.5; 5.3) | 1.65(ddd) (13.0; 3.5; 5.4) | 1.70(ddd) (13.0; 3.35; 5.0) | 1.66(ddd) (13.0; 3.8; 5.8) |
| 16-H | 1.28(d) (13.2) | 1.32(d) (13.0) | 1.30(d) (13.0) | 1.32(d) (13.0) | 1.25(d) (13.27) |
| 17-H | 2.40 (5.0) | 2.38(d) (5.0) | 2.36(d) (5.0) | 2.40(d) (5.0) | 2.34(d) (5.03) |
| 18-H | 1.95(s) | 2.05(s) | 1.198(s) | 2.08(s) | 1.93(s) |
| 19-H | 3.58(d) (9.6) | 3.62(s) (8.0) | 3.60(d) (8.5) | 3.62(d) (9.2) | 3.77(s) |
| 19-H | 4.00(d) (9.6) | 3.62(s) (8.0) | 4.02(d) (8.5) | 3.90(d) (9.2) | 3.77(s) |
| 21-H | 5.65(s) | 5.64(s) | 5.60(s) | 5.60(s) | 5.63(s) |
| 22-H | 5.05(d) (2.9) | 5.00(d) (2.9) | 5.0(d) (2.9) | 5.06(d) (2.85) | 5.03(d) (2.9) |
| 23-H | 6.40(d) (2.9) | 6.42(d) (2.9) | 6.42(d) (2.9) | 6.44(d) (2.85) | 6.48(d) (2.9) |
| 28-H | 4.02(d) (9.0) | 3.80(d) (7.6) | 4.16(d) (7.8) | 4.06(d) (9.0) | 4.06(d) (8.76) |
| 28-H | 3.80(d) (9.0) | 3.70(d) (7.6) | 3.80(d) (7.8) | 3.74(d) (9.0) | 3.72(d) (8.8) |
| 29-H | — | 1.04(s) | — | — | — |
| 30-H | 1.76(s) | 1.74(s) | 1.73(s) | 1.42(s) | 1.29(s) |
| 7-CH | — | 2.78(brs) | — | — | 2.8(brs) |
| 11-CH | — | 5.00(s) | — | — | 3.26(br.s) |
| 14-CH | — | 3.06(br.s) | — | — | 3.06(br.s) |
| 12-OCH$_3$ | 3.65(s) | — | 3.65(s) | 3.68(s) | — |
| 29-OCH$_3$ | 3.76(s) | 3.77(s) | 3.75(s) | 3.78(s) | 3.77(s) |
| CH$_3$COO | 1.84(s) | 1.83(s) | 1.93(s) | 2.02(s) | 1.83(s) |
| Tigloyl | 6.88(qq) | 6.95(qq) | Benzoyl gr. | — | (7.0; 1.34) |
| 3'-H | (7.0; 1.3) | (7.0; 1.3) | 2'-7.9(m) 6'-7.7(m) | — | (7.0; 1.34) |
| 4'-H | 1.76(dq) (7.0; 1.01) | 1.74(dq) (7.0; 1.01) | 3'-7.57(m) 4'-7.4(m) 5'-7.6(m) | — | 1/74(dq) (7.06, 1.01) |
| 5'-H | 1.84(dq) (1.5, 1.01) | 1.81(dq) (1.5, 1.01) | — | — | 1.81(dq) (1.5; 1.01) |

| Compound No. | 7 | 8 | 9 | 10 | 11 |
|---|---|---|---|---|---|
| 1-H | 4.93(t) (2.9; 3.1) | 4.60(t) (2.85; 3) | 3.74(t) (2.9; 3.0) | 4.72(t) (2.9; 3.1) | 3.62(dd) (2.9; 3.0) |
| 2-H | 2.38(ddd) (16.0; 2.9; 2.7) | 2.33(ddd) (16.0; 2.7; 2.8) | 2.36(ddd) (16.0; 2.6; 2.8) | 2.28(ddd) (16.2, 2.9, 2.6) | 2.76(ddd) (16.2; 2.9; 2.65) |
| 2-H | 2.14(ddd) (16.0; 2.7; 2.8) | 2.14(ddd) (16.0; 2.7; 2.8) | 2.16(ddd) (16.0; 2.6; 2.8) | 2.13(ddd) (16.2; 2.6; 2.9) | 2.12(ddd) (16.2; 2.6; 2.85) |
| 3-H | 5.30(t) (2.9; 3.1) | 5.15(dd) (2.9; 3.1) | 5.45(t) (2.9; 3.0) | 5.48(t) (2.9; 3.0) | 3.76(t) (2.8; 3.2) |
| 5-H | 3.10(d) (12.5) | 3.30(d) (12.5) | 3.30(d) (12.5) | 3.30(d) (12.5) | 3.16(d) (12.5) |
| 6-H | 4.04(dd) (12.5; 3) | 4.04(dd) (12.5; 3.0) | 4.13(dd) (12.5; 3) | 4.42(dd) (12.5; 3.2) | 4.16(d) (12.5; 3.0) |
| 7-H | 4.65(s) (3.0) | 4.44(d) (3.0) | 4.64(d) (3.20) | 4.48(d) (3.2) | 4.62(d) (3.0) |

$^1$H-NMR DATA OF COMPOUND 2–11 (CHART-1) -continued

| Serial No. | 2 | 3 | 4 | 5 | 6 |
|---|---|---|---|---|---|
| 9-H | 2.60(s) | 4.24(s) | 4.02(s) | 3.48(S) | 4.02(s) |
| 11-H | 3.75(m) | — | — | — | — |
| | — | 3.85(d)(14.0) | — | — | — |
| 12-H | 3.92(br.s) | 5.40(d)(14.0) | — | — | — |
| 15-H | 4.55(d) (3.2) | 4.62(d) (3.2) | 4.2(d) (3.0) | 4.18(m) | 4.60(d) (3.0) |
| 16-H | 1.60(ddd) (13.0;, 3.4; 5.0) | 1.60(ddd) (13.0; 3.4; 5.0) | 1.67(ddd) (13.0; 3.4; 5.1) | 1.80(m) | 1.65(m) |
| 16-H | 1.26(ddd) (13.0) | 1.26(d) (5.0) | 1.30(d) (5.0) | 1.90(m) | 1.92(m) |
| 17-H | 2.40(d) (5.0) | 2.58(d) (5.0) | 2.42(d) (5.0) | 2.16(m) | 2.14(m) |
| 18-H | 2.00(s) | 1.98(s) | 2.07(s) | 1.55(s) | 2.04(s) |
| 19-H | $CH_3$-1.32(s) | 1.23(s) | 1.40(s) | 3.66(d) (9.7) | $CH_3$-1.45(s) |
| 19-H | | | | 4.28(d) (9.7) | |
| 21-H | 5.62(s) | 5.60(s) | 5.62(s) | 5.65(s) | 5.62(s) |
| 22-H | 5.05(d) (2.90) | 5.05(s) (2.90) | 5.04(s) (3.0) | 4.88(s) (2.9) | 1.88(s) (2.9) |
| 23-H | 6.40(d) (2.90) | 6.40(d) (2.90) | 6.40(d) (3.0) | 6.36(d) (2.9) | 6.36(d) (2.9) |
| 28-H | 3.70(br.s) | 4.55(s) | 3.72(d) (9.6) | 3.69(d) (8.8) | 3.65(d) (8.6) |
| 28-H | 3.70(br.s) | 3.85(d) (9.0) | 3.60(d) (9.0) | 4.04(d) (8.8) | 3.92(d) (8.5) |
| 29-H | 1.05(s) | — | — | — | — |
| 30-H | 1.58(s) | 1.68(s) | 1.73(s) | 1.68(s) | 1.60(s) |
| 7-CH | — | 2.58(br.s) | 2.8(br.s) | — | — |
| 11-CH | — | — | — | — | — |
| 14-CH | — | 2.92(br.s) | 2.95(br.s) | — | — |
| 12-$OCH_3$ | — | — | — | 3.68(s) | 3.68(s) |
| 29-$OCH_3$ | — | 3.72(s) 1.98(s) | 3.78(s) | 3.76(s) | 3.78(s) |
| $CH_3COO$ | 1.86(s) | 1.92(s) | 2.02(s) | 1.98(s) | — |
| Tigloyl 3'-H | 6.93(qq) (7.0; 1.34) | 6.94(qq) (7.0; 1.30) | — | 6.88(qq) (7.0; 1.3) | — |
| 4'-H | 1.78(dq) (7.0; 1.1) | 1.78(dq) (7.0; 1.1) | — | 1.75(dq) (7.0; 1.1) | — |
| 5'-H | 1.83(dq) (1.34; 1.1) | 1.84(dq) (1.30; 1.1) | — | 1.84(dq) (1.3; 1.11) | — |

$^{13}$C-NMR DATA COMPOUND 3 AND 6 (CHART-2)

| | 3 | 6 |
|---|---|---|
| C-1 | 70.8478(d) | 72.928(d) |
| C-2 | 29.5797(t) | 29.577(t) |
| C-3 | 68.9088(d) | 67.115(d) |
| C-4 | 42.3927(s) | 52.3129(s) |
| C-5 | 35.663(d) | 36.998(d) |
| C-6 | 74.9161(d) | 72.215(d) |
| C-7 | 76.4206(d) | 74.018(d) |
| C-8 | 44.9545(s) | 43.335(s) |
| C-9 | 44.7298(d) | 48.499(d) |
| C-10 | 49.8957(s) | 47.760(s) |
| C-11 | 103.9192(s) | 100.911(d) |
| C-12 | 171.6262(s) | — |
| C-13 | 69.9268(s) | 66.917(s) |
| C-14 | 69.9220(s) | 69.946(s) |
| C-15 | 76.2910(d) | 76.147(d) |
| C-16 | 24.9646(t) | 25.255(t) |
| C-17 | 48.8888(d) | 48.132(d) |
| C-18 | 18.2318(q) | 18.570(q) |
| C-19 | 72.5881(t) | 72.928(t) |
| C-20 | 83.4946(s) | 83.384(s) |
| C-21 | 108.8309(d) | 108.545(d) |
| C-22 | 107.2595(d) | 107.509(d) |
| C-23 | 146.8451(d) | 147.074(d) |
| C-28 | 77.35(t) | 77.425(t) |
| C-29 | 18.9414(q) | 173.428(s) |
| C-30 | 21.0782(q) | 20.824(q) |
| $COOCH_3$ | 53.0748(q) | 52.452(q) |
| $CH_3COO$ | 169.7945(s) | 169.657(s) |
| $CH_3COO$ | 20.7701(q) | 2.485(q) |
| OTig; | | |
| C-1' | 166.1988(s) | 166.510(s) |
| C-2' | 128.6384(s) | 128.689(s) |
| C-3' | 137.1983(d) | 137.941(d) |
| C-4' | 14.1673(q) | 14.237(q) |
| C-5' | 11.8579(q) | 11.804(q) |

According to a feature of the invention, there is provided a process for the preparation of new insecticidally active compositions containing the above referred new triterpenes including azadirachtin and its derivatives from the neem plant which process comprises:

a. grinding the parts of the neem plants to get a powder;

b. extracting the powder with a binary immiscible solvents consisting of one polar and the other non-polar solvent in the ratio of 1:2 to obtain an extract;

c. filtering the resultant extract to get a filtrate having two layers one layer containing lipids, and other containing the new triterpenes including azadirachtin and its derivatives and water soluble constituents including sugars;

d. separating the layers by known methods;

e. concentrating the layer containing triterpenes including the azadirachtin and its derivatives and water soluble constituents including sugars;

f. treating the resultant concentrate with a polar solvent and g. filtering the resultant solution to produce a filtrate containing the mixture of new triterpenes including azadirachtin and its derivatives.

It is found that the fraction in the polar solvent phase consists of triterpenes, azadirachtin and its derivatives in the range of 40–60% along with some water soluble compounds such as sugars, glucosides, and amino acids. The non-terpenenic portion which has been found to be water soluble can easily be removed from the terpenic portion by any known methods such as by partitioning between water and water immiscibie polar solvents. Examples of water immiscible polar solvents which can be used are ethylenedichloride, chloroform, carbontetrachloride, n-butanol, isobutanol and the like. Alternatively, the triterpenic active fraction can be separated by dissolving it in polar solvents like ethylenedichloride, ethylacetate, acetone and chloroform. The final triterpene fraction obtained by this method amounts to 2–5% based on the seed powder. This fraction contains at least 35 triterpenes related to azadirachtin of which 25–30 are biologically active. The known triterpenes include salannin, gedunin, azadiradione, azadirone, salannol acetate, epoxyazadiradione, nimbandiol, salannin derivatives, salannol derivatives, azadirchtin and new derivatives of azadirachtin. All these compounds are found to exhibit insect antifeedant and growth inhibitory activities.

The lipid fraction (i.e. the layer containing the lipids) obtained during partitioning in the non-polar solvent i.e. step c) consists of mono-, di- and triglycerides of fatty acids, sulphur compounds, straight chain hydrocarbons, straight chain esters of fatty alcohols ana acids, phyosterols and their esters and less polar triterpenes and free fatty acids of the type, oleic, stearic, linoleic, arachidoic and tiglic is found to exhibit insecticidal activity against soft bodied insects and sucking pests such as aphids, mites, cotton white fly, jassids, etc. The activity of the fraction is enhanced by dissolving the total lipid fraction in a polar solvent and chilling the resultant solution to a temperature in the range of 0°–10° C. for a period ranging from 10–20 hrs. The solid separating out under the above conditions is filtered and the solvent removed from the filtrate preferably by distillation to give the active fraction. This active fraction consisting of enriched unsaturated lipids is found to constitute 8–12% based on the seeds and in the case of neem cake it is found to be 4–6%.

The liquid fraction (2 kg) was dissolved in acetone (3 liters) and the solution was chilled at 0° to −10° C. for 12 hrs. The chilled product was filtered quickly and the filtrate was concentrated by distilling acetone and the residue obtained weighed 1 kg. It consists of mostly unsaturated fatty acids, unsaturated glycerides, hydrocarbons, sulphur compounds, phytosterols (sitosterol, stigmsterol, campesterol) and less polar triterpenes such as gedunin, azadirone, zadirodione, nimbin, deacetylnmibin etc.

According to another embodiment of the present invention there is provided a process for the preparation of a new insecticidally active composition containing lipids enriched with unsaturated fats from the part of the neem plant which comprises:

a. grinding the parts of the neem plant to get a powder;

b. by extracting the powder with a mixture of two immiscible solvents consisting of one polar and other non-polar in the ratio of 1:2 to obtain an extract;

c. filtering the resultant extract to get a filtrate having two separable layers, one layer containing the lipids and the other containing the triterpenes including azadirachtin and the derivatives of azadirachtin and water soluble constituents including sugars;

d. separating the layers by known methods;

e. concentrating the non-polar solvent layer containing the lipids to obtain the total lipids and f. dissolving the above lipids in a polar solvent and chilling the solution in the range of 0° to −10° C. for 12 hrs and filtering to produce a filtrate containing unsaturated lipids.

By way of examples the polar solvents which can be employed are chloroform, ethanol, methanol, isobutanol, n-butanol, ethylenedichloride and the like. The non-polar solvents which can be used are selected from hexane, heptane, pentane, benzene, toluene and the like.

The present invention is illustrated by the examples given below which should not be constructed to limit the scope of the invention.

EXAMPLE 1

Neem seeds which were stored at least for 2–4 months after collection were powdered and 10 kg of the powder was stirred with 30 liters of methanol:hexane (1:2) for 2 hours and filtered. The filtrate containing two layers, one of methanol and the other of hexane were separated and the solvents removed from both the layers to yield the triterpenes along with water soluble polar compounds 0.7 kg. The lipid portion weighed 1.8 kg. 0.7 kg of the methanol extract was treated with warm (about 40° C.) acetone and decanted. The clear solution was stripped off the solvent to give triterpene-rich insect control agents, 250 g.

The triterepene active fraction (120 g) was separated by using column grade Silica gel (60–120 mesh size) and acetone:pet-ether solvent mixture with increasing percentage of acetone as the elution gradient was used to collect four broad fractions A (25 g), B (32 g), C (45 g) and D (18 g).

Rechromatography of fraction D (18 g) on Silica gel using ethyl acetate-benzene with increasing polarity of ethyl acetate resulted in five broad fractions D1 (4 g), D2 (6 g), D3 (1.5 g), D4 (2 g) and D5 (4.5 g). D3 (1.5 g) fraction was again rechromatographed on Silica gel (60–120 mesh) with chloroform:methylcyanide as the eluent with the increasing percentage of methylcyanide to give the mixture of compounds (2), (4), (8), (9) and (10) along with less polar and more polar compounds. Preparative TLC on Silica gel (400 mesh) of this fraction with ethylacetate benzene (9:1) enriched the above (2), (4), (8), (9) and (10) compounds. The enriched fraction containing the above compounds was separated by preparative TLC Silica gel (400 mesh size) with chloroform:methylcyandie (5:2) as the solvent system gave each compound 75% purity. Again each compound was purified by preparative TLC (Silica gel, 400 mesh) with acetone:pet-ether (4:6) as solvent system gave the pure compounds (2), (4), (8), (9) and (10).

$D_4$ (2 g) fraction was again subjected to column chromatography over column grade Silica gel (80–120 mesh) using ethylacetate:benzene with increasing percentage of ethylacetate which gave a crude mixture of five more polar compounds (3) (5), (6), (7) and (11) along with the less and more polar minor components. The above crude mixture was put on preparative TLC (Silica gel, 400 mesh size) with chloroform:methylcyanide (5:2) which gave each compound in 50% pure form. Each of the above 50% pure compounds was again loaded on preparative TLC (Silica gel, 400 mesh size) with acetone:pet-ether (4:6) to enrich it to 90% purity and again each was finally purified to obtain all the more polar compounds (3), (5), (6), (7) and (11) by using ethylacetate:benzene (9:1) as solvent system on preparative TLC (400 mesh size, Silica gel).

EXAMPLE 2

Neem seeds which were stored at least for 2–4 months after collection were powdered and 10 kg of the powder was stirred with 30 liters of methanol:hexane (1:2) for 2 hours and filtered. The filtrate containing two layers, one of methanol and other of hexane were separated and the solvents removed from both the layers to yield the triterpenes along with water soluble polar compounds 0.7 kg. The lipid portion weighed 1.8 kg. 0.7 kg of methanol extract was treated with warm (about 40° C.) acetone and decanted. The clear solution was stripped off the solvent to give triterpene-rich pest control agents 250 g.

The triterpenes-active fraction (150 g) was separated by using column grade Silica gel (60–120 mesh size) and acetone:pet-ether solvent system with increasing percentage of acetone as the elution gradient to collect four broad fractions A (30 g), B (42 g), C (55 g) and D (26 g).

Rechromatography of fraction D (26 g) on Silica gel (60–120 mesh) using chloroform:methylcyanide resulted in five broad fractions $D_1$ (9 g), $D_2$ (4 g), $D_3$ (4 g), $D_4$(5 g) and $D_5$(4 g).

$D_3$ (4 g) fraction was again put on column for further separation over Silica gel (60–120 mesh size) with acetone:pet-ether with increasing percentage of acetone which gave the mixture of (2), (4), (8), (9) and (10) along with less and more polar constituents. Preparative TLC of this mixture on Silica gel (400 mesh size) enriched the above five compounds (2), (4), (8), (9) and (10) with ethylacetate::benzene (9:1) to 50% purity. The enriched fraction containing the above compounds was further separated by preparative TLC on Silica gel (400 mesh size) with chloroform:methylcyanide as solvent system (5:2) to give each of the above compounds in 75% purity. Again each one was purified on preparative TLC (Silica gel, 400 mesh size) with acetone:pet-ether (4:6) which gave the pure compounds.

$D_4$ (4 g) fraction was again subjected to column chromatography over column grade Silica gel (60–120 mesh) using chloroform:methylcyanide with increasing percentage of methylcyanide which gave a crude mixture of five more polar compounds (3), (5), (6), (7) and (11) along with the less and more polar compounds. The above crude mixture was separated on preparative TLC (Silica gel, 400 mesh size) with ethylacetate:benzene (9:1) which gave each compound in 50% pure form. The above 50% was again loaded on preparative TLC (Silica gel, 400 mesh size) with chloroform:methylcyanide (5:2) to give 90% pure compounds and finally they were purified by preparative TLC using acetone:pet-ether (4:6) to get very pure compounds viz. (3), (5), (6), (7) and (11).

The antifeedant activity of all the compounds was evaluated as follows:

A test solution containing 20 ppm of each compound was prepared. Weighed discs of leaves were treated with the above solution and the larvae of *Heliothis armigera* were released on these treated leaves. A untreated control experiment was run simultaneously. The weight of the leaves after 24 hrs and 48 hrs were recorded to evaluate the antifeedant activity of the compounds. Table 1 shows antifeedant activity of compounds 3,5 and 6.

TABLE 1

| Compound of | % Protection | |
|---|---|---|
| the formula | After 24 hr | After 48 hr |
| 3 | 50 | 60 |
| 5 | 50 | 60 |
| 6 | 75 | 80 |

EXAMPLE 3

Neem seeds which were stored for at least 2–4 months after collection, were powdered and 10 kg of the powder was stirred with 30 liters of methanol:hexane (1:2) for 2 hrs and filtered. The filtrate containing two layers, one of the methanol and the other of hexane were separated by using a separatory funnel and the solvents removed from both the layers to yield triterpenes including azadirachtin and its derivatives along with water soluble polar compounds weighing 0.7 kg. The lipid portion weighed 1.8 kg.

0.7 kg of the aqueous methanol extract was treated with 7 liters of warm acetone (35°–40° C.) in three lots and the acetone solubles were decanted and the solvent removed to yield the triterpene active fraction weighing 250 gms. The residue (450 gms) which was insoluble in acetone was discarded. Azadirachtin content in the above triterepene active mixture was estimated by HPLC using (60:40) methanol:water 1 ml/ml C-18 reverse phase column and 215 nm UV detector. Azadirachtin peak was identified by comparing with that of authentic sample and the percentage of azadirchatin was found to be 8%.

EXAMPLE 4

Neem cake (10 kg) obtained by expelling the oil in an expeller was stirred with 90% aq. methanol and hexane (30 liters, 1:2) for 2 hrs and filtered. The aqueous methanol layer and the hexane layer were separated in a separatory funnel and the solvents removed separately to give 0.8 kg of the aqueous methanol solubles and 0.8 kg of lipid fraction respectively.

The aqueous methanol solubles 0.8 kg was shaken with 10 liters of isobutanol and water (1:1) and isobutanol layer was separated in a separatory funnel which was distilled off to give triterpene active fraction, 280 gms.

Azadirachtin content of the above triterpene active fraction using HPLC (50:50, methanol:water, 1 ml/ml C-18 reverse phase column) and the UV detector at 217 nm was found to be 10%.

EXAMPLE 5

Neem seed powder (10 kg) was extracted with stirring with a mixture of aqueous methanol (85%) and heptane (30 liters, 1:2) and filtered. The filtrate consisting of both aqueous methanol and heptane layers was separated in a separatory funnel and the solvents removed to give aqueous methanol solubles (0.75 kg) and the lipid fraction in the heptane solubles (2.0 kg).

Methanol solubles (0.75 kg) were partitioned between ethylenedichloride and water (3 liters each) and the ethylenedichloride layer was separated and concentrated to give 250 gms of triterpene active fraction. Azadirachtin content using HPLC at 215 nm UV wavelength and acetonitrile:water (60:40) 1 ml/ml C-18 reverse phase column was found to be 9%.

Figure 5:
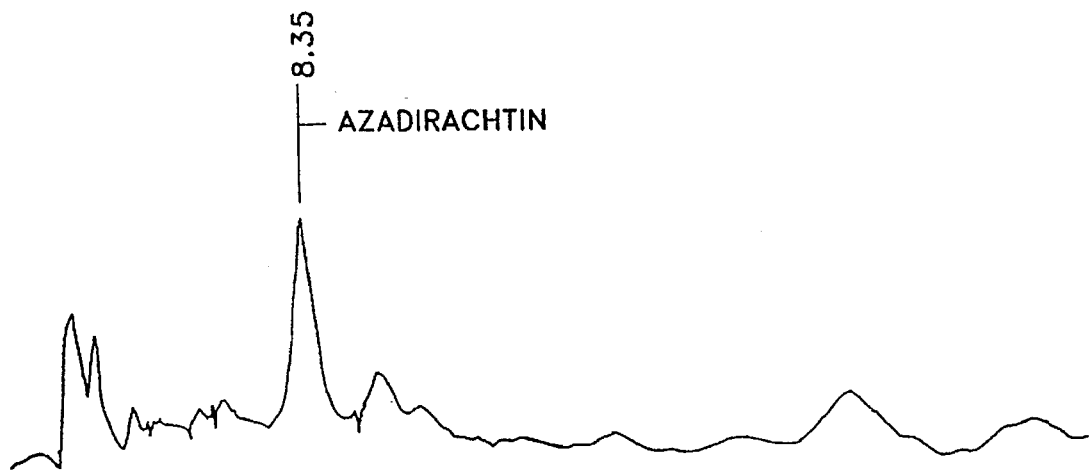
FIG. 5—is the HPLC chromatogram of the triterpene active fraction.

1. The HPLC chromatogram of the triterpene active fraction is depicted in FIG. 5.
2. The bioefficacy data generated for triterpene active fraction at 1000 ppm are given in Table 2.

TABLE 2

BIOEFFICACY DATA OF TRITERPENE ACTIVE FRACTION DURING FIELD TRIALS ON VARIOUS CROPS AND COMPARISON WITH OTHER NEEM BASED INSECT-CONTROL AGENTS.

Tobacco nursery Plot size: 6 m × 1 m

| | No. of seedlings damaged by larvae of Spodoptera litura Days after spraying | |
|---|---|---|
| Product | 2 | 9 |
| 1. Triterpene active fraction | 3.04 | 2.50 |
| 2. Commercial sample 1 | 3.27 | 3.44 |
| 3. Commercial sample 2 | 3.50 | 3.08 |
| 4. Commercial sample 3 | 4.77 | 5.31 |
| 5. Control | 8.37 | 8.91 |

Mustard Plot size: 6 m × 6 m

| Product | Yield (Quintal/Hectare) |
|---|---|
| 1. Triterpene active fraction | 14.5 |
| 2. Commercial sample 1 | 13.7 |
| 3. Commercial sample 4 | 11.7 |
| 4. Control | 9.5 |

Cotton Plot size: 8 m × 8 m

Percentage bud damage due to spotted bollworm *Erias vittella*; percentage boll damage due to pink bollworm *Pectinophora gossipiella* and seed cotton yield (Quintal/hectare).

| Product | % bud damage | % boll damage | Yield |
|---|---|---|---|
| 1. Triterpene active fraction | 32.1 | 25.4 | 18.9 |
| 2. Commercial sample 1 | 32.6 | 26.5 | 17.7 |
| 3. Commercial sample 3 | 39.7 | 32.7 | 14.6 |
| 4. Control | 45.4 | 38.5 | 11.7 |

Safflower Plot size: 5 m × 5 m

Percentage of capitula damage due to *Helithis armigera* and yield (Quintal/hectare)

| Product | % Capitula damage | Yield |
|---|---|---|
| 1. Triterpene active fraction | 26.5 | 15.4 |
| 2. Commercial sample 1 | 30.4 | 13.6 |
| 3. Commercial sample 4 | 36.5 | 12.7 |
| 4. Control | 52.5 | 11.4 |

Sorghum Plot size: 6 m × 6 m

Dead heart percentage due to shootfly *Atherigona Soccata*, and sorghum stem borer *Chilo pertellus*.

| Product | % Dead heart 21st day | % Dead heart after 28 days | % Dead heart due to stem borer. |
|---|---|---|---|
| 1. Triterpene active fraction | 21.8 | 32.7 | 10.6 |
| 2. Commercial sample 1 | 25.4 | 36.9 | 14.7 |
| 3. Commercial sample 3 | 26.5 | 37.6 | 17.6 |
| 4. Control | 35.6 | 42.8 | 38.5 |

TABLE 2-continued

Sorghum: GRAIN AND FODDER YIELD

| Product | Grain yield Quintal/hectare | Fodder yield Tonne/hectare |
|---|---|---|
| 1. Triterepene active fraction | 16.1 | 8.7 |
| 2. Commercial sample 1 | 14.3 | 6.9 |
| 3. Commercial sample 3 | 12.5 | 6.7 |
| 4. Control | 8.6 | 5.4 |

EXAMPLE 6

Neem seeds which were stored for at least 2-4 months after collection were powdered and 10 kg of the powder was stirred with 30 liters of aqueous (85%) methanol:hexane (1:2) for 2 hours and filtered. The filtrate containing two layers one of methanol and other of hexane were separated and the solvents removed from both the layers to yield the triterpenes along with water soluble polar compounds 0.7 kg and 1.8 kg of the lipid fraction respectively.

The lipid fraction (1 kg) was dissolved in acetone (1.5 liters and chilled to 0° to −10° C. for 12 hrs. The solid separated was filtered at 0° C. and the filtrate containing the unsaturated lipids was concentrated to give the lipid-active fraction, 0.5 kg. The saturated fats were used for other purposes.

EXAMPLE 7

Neem cake obtained by the expelling oil in an expeller (20 kg) was stirred with 85% aqueous methanol and hexane (60 liters) (1:2) for three hours and filtered. The aqueous methanol layer and the hexane layer were separated and solvent removed separately to give 1.6 kg of mixture of triterpenes and water soluble polar compounds and 1.6 kg of lipid fraction.

The lipid fraction (1 kg) was dissolved in 1 liter of ethylene dichloride and chilled to 0° to −10° for 12 hrs and the solid separated was filtered. The filtrate containing the unsaturated lipids were concentrated to give the lipid active fraction 0.450 kg. The saturated fats were used for other purposes.

EXAMPLE 8

Neem seeds which were stored at least for 2-4 months after collection were powdered and 10 kg of the powder was stirred with 30 liters of methanol:hexane (1:2) for 2 hours and filtered. The filtrate containing two layers one of methanol and other of hexane were separated and the solvents removed from both the layers to yield the triterpenes along with water soluble polar compounds 0.7 kg and 1.8 kg of the lipid fraction respectively.

The lipid fraction (1 kg) was dissolved in 1 liter of ethylacetate and chilled at 0° to −10° C. for 12 hrs. The solid separated was removed by filtration at 0° and the filtrate which contained unsaturated lipids was concentrated to give the lipid active fraction, 0.6 kg. The saturated fats were used for other purposes.

The bioefficacy data generated during field trials at 400 ppm with lipid-active fraction on different aphids on various crops are given in Table 3 which also also shows a comparative bioefficacy with those of some neem pesticides.

TABLE 3

BIOEFFICACY DATA OF LIPID-RICH ACTIVE FRACTION DURING FIELD TRIALS AGAINST DIFFERENT APHIDS ON VARIOUS CROPS.
(Number denotes the average number of apids/5 plants).

| Day after spray | Lipid active Fraction | Margosan-O | Neemark |
|---|---|---|---|
| Precount 1st spray | 48.7 | 48.2 | 46.2 |
| 1 | 40.0 | 31.2 | 40.2 |
| 2. | 31.2 | 27.7 | 30.2 |
| 4. | 18.7 | 27.0 | 35.2 |
| 10. | 16.2 | 28.2 | 37.7 |
| 14 | 22.2 | 30.0 | 37.0 |
| 15 second spray | | | |
| 1 | 17.7 | 24.7 | 20.2 |
| 2 | 15.0 | 18.5 | 25.0 |
| 4 | 15.2 | 27.2 | 27.7 |
| 10 | 16.2 | 35.7 | 30.5 |
| 14 | 22.2 | 38.2 | 37.2 |
| 15 Third spray | | | |
| 1 | 17.2 | 31.2 | 30.2 |
| 2 | 20.2 | 27.7 | 40.7 |
| 4 | 22.0 | 29.5 | 47.0 |
| 10 | 22.7 | 31.7 | 57.0 |
| 14 | 23.7 | 37.5 | 57.0 |
| 15 Fourth spray | | | |
| 1 | 17.7 | 22.2 | 47.2 |
| 2 | 20.7 | 27.5 | 45.0 |
| 4 | 22.5 | 30.7 | 48.2 |
| 10 | 22.5 | 30.0 | 56.2 |
| 14 | 22.0 | 35.0 | 59.0 |

Mustard Aphid *Lipaphis erysimi*; 1 plot size 6 m × 6 m
Mustard sawfly: *Athalia proxima* 2.

| Day after spray | Lipid active Fraction | | Margosan-O | | Jawan | |
|---|---|---|---|---|---|---|
| | 1 | 2 | 1 | 2 | 1 | 2 |
| Precount First spray | 38 | 11 | 34 | 13.2 | 38 | 11 |
| 1 | 20 | | 22 | | 28 | |
| 2 | 17 | | 18 | | 26 | |
| 4 | 15 | | 18 | | 30 | |
| 10 | 15 | | 18 | | 32 | |
| 14 | 16 | | 21 | | 37 | |
| 15 Second spray | | | | | | |
| 1 | 12 | 7 | 17 | 7 | 30 | 10 |
| 2 | 12 | 7 | 17 | 7 | 27 | 10 |
| 4 | 10 | 7 | 15 | 7 | 29 | 10 |
| 10 | 11 | 8 | 15 | 8 | 31 | 10 |
| 14 | 12 | 8 | 16 | 8 | 34 | 11 |
| 15 Third spray | | | | | | |
| 1 | 13 | 5 | 10 | 6 | 35 | 9 |
| 2 | 13 | 5 | 11 | 6 | 30 | 9 |
| 4 | 15 | 6 | 11 | 7 | 32 | 9 |
| 10 | 15 | 7 | 11 | 7 | 37 | 9 |
| 14 | 17 | 7 | 13 | 7 | 39 | 10 |
| 15 Fourth spray | | | | | | |
| 1 | 12 | 5 | 10 | 6 | 27 | 8 |
| 2 | 10 | 5 | 11 | 6 | 25 | 8 |
| 4 | 11 | 6 | 12 | 7 | 29 | 9 |
| 10 | 11 | 6 | 12 | 7 | 34 | 9 |
| 14 | 13 | 6 | 15 | 8 | 39 | 11 |

TABLE 3-continued

BIOEFFICACY DATA OF LIPID-RICH ACTIVE FRACTION DURING FIELD TRIALS AGAINST DIFFERENT APHIDS ON VARIOUS CROPS.
(Number denotes the average number of apids/5 plants).

Safflower Aphid: *Daetynotus carthami* Plot size 5 m × 5 m

| Day after spray | Lipid active Fraction | Margosan-O | Jawan |
|---|---|---|---|
| Precount First spray | 37 | 39 | 37 |
| 1 | 24 | 22 | 30 |
| 2 | 21 | 17 | 27 |
| 4 | 17 | 17 | 25 |
| 10 | 18 | 18 | 21 |
| 14 | 18 | 15 | 37 |
| 15 Second spray | | | |
| 1 | 8 | 8 | 28 |
| 2 | 6 | 8 | 20 |
| 4 | 6 | 9 | 18 |
| 10 | 7 | 13 | 19 |
| 14 | 6 | 14 | 27 |
| 15 Third spray | | | |
| 1 | 3 | 9 | 20 |
| 2 | 3 | 9 | 17 |
| 4 | 4 | 9 | 17 |
| 10 | 6 | 11 | 22 |
| 14 | 6 | 13 | 26 |
| 15 Fourth spray | | | |
| 1 | 1 | 7 | 18 |
| 2 | 4 | 7 | 17 |
| 4 | 4 | 11 | 11 |
| 10 | 6 | 14 | 22 |
| 14 | 7 | 16 | 26 |

Sorghum Apid: *Schizophis Sorshiella* Plot size 6 m × 6 m

| Day after spray | Lipid active Fraction | Margosan-O | Neemark |
|---|---|---|---|
| Precount Third spray | 31.5 | 36.5 | 39.5 |
| 1 | 16.2 | 30.2 | 30.2 |
| 2 | 16.0 | 26.2 | 27.7 |
| 5 | 17.2 | 24.2 | 22.5 |
| 10 | 18.2 | 26.7 | 28.5 |
| 14 | 19.2 | 29.5 | 29.2 |
| 15 Fourth spray | | | |
| 1 | 13.5 | 21.7 | 21.5 |
| 2 | 14.5 | 21 | 17.7 |
| 5 | 14.0 | 23.7 | 21.5 |
| 10 | 15.2 | 26.3 | 24.7 |
| 14 | 15.5 | 28.2 | 29.2 |

Figure 2:
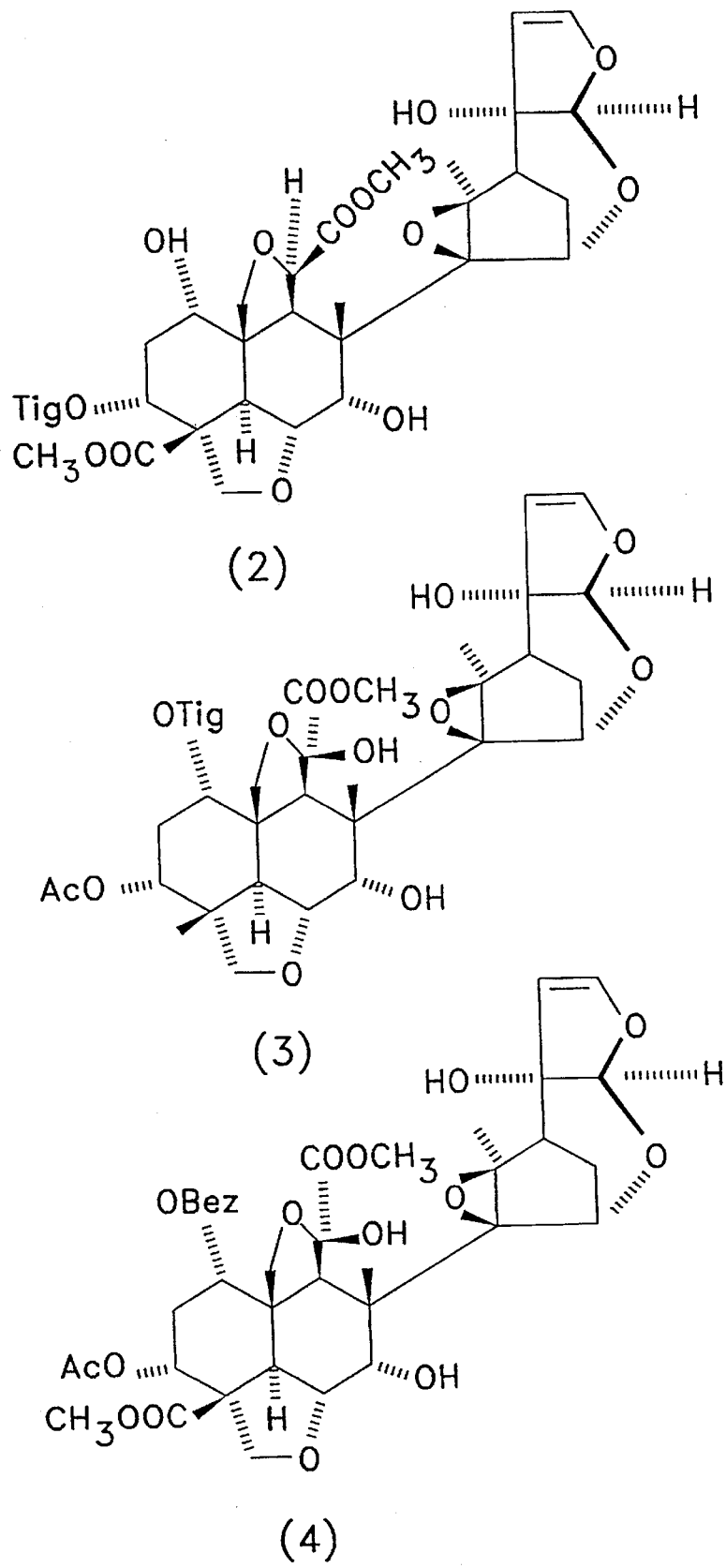
FIG. 2—shows triterpenes of Formulas 2–4.
Figure 3:
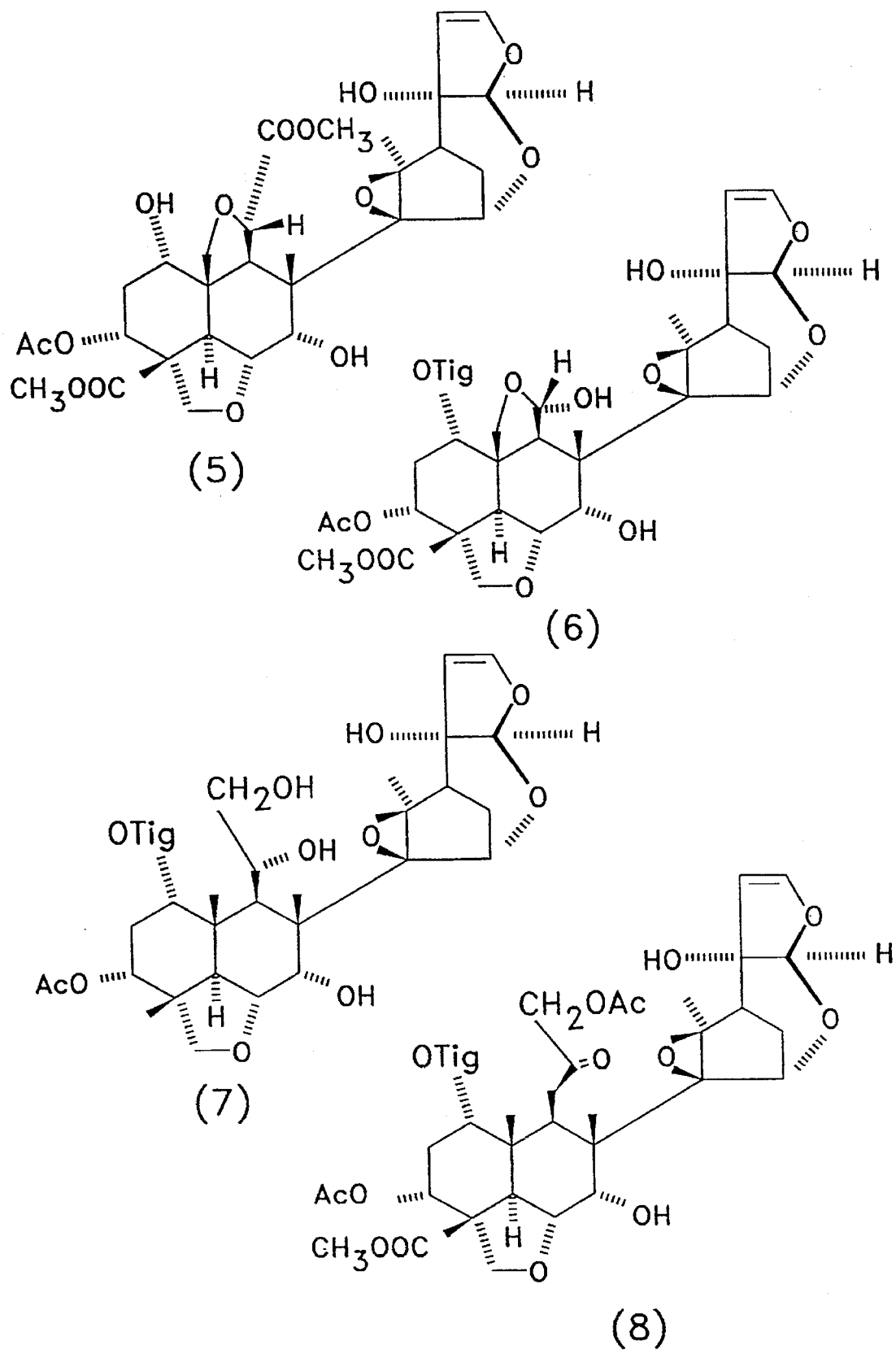
FIG. 3—shows triterpenes of Formulas 5–8.
Figure 4:
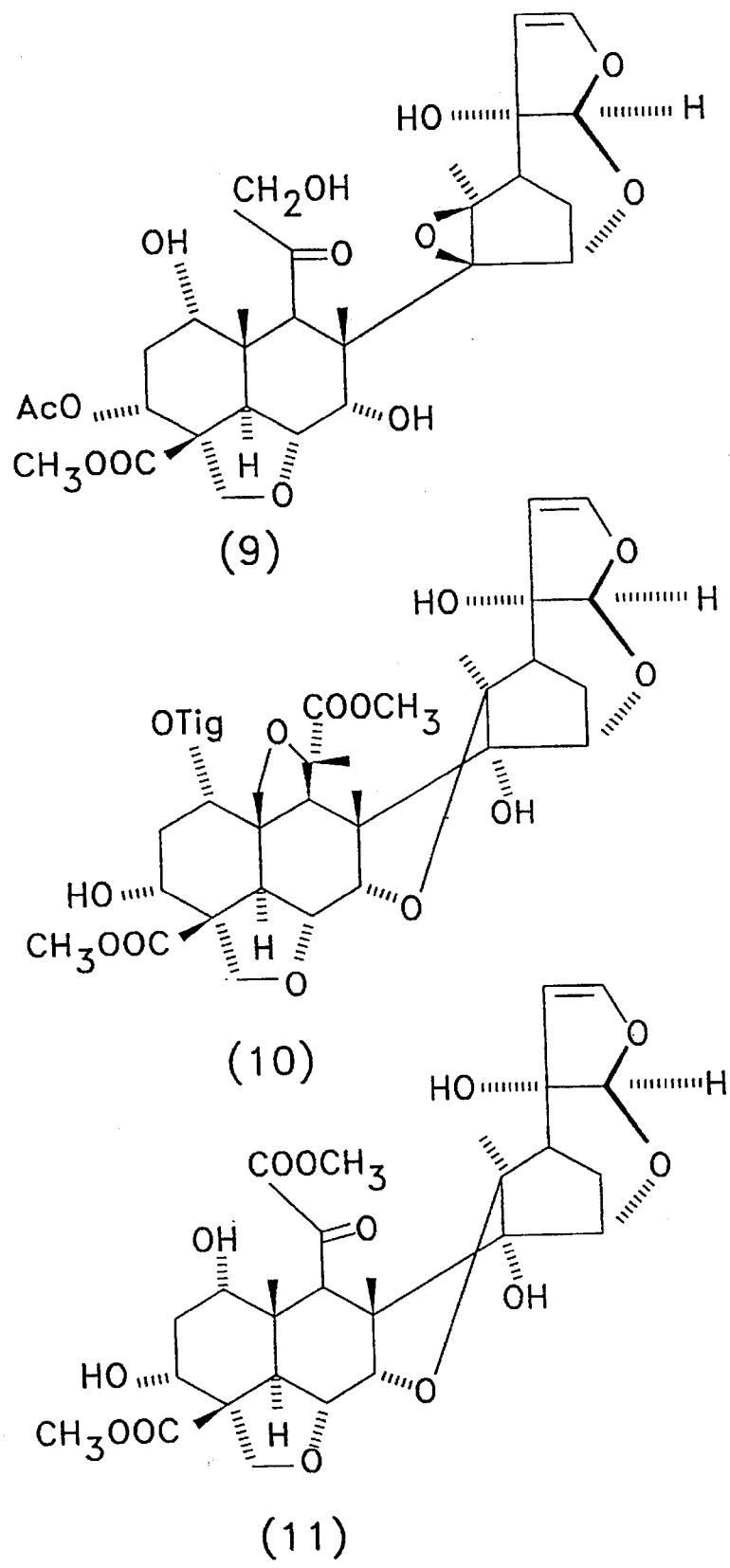
FIG. 4—shows triterpenes of Formulas 9–11.

We claim:

1. A process for isolation of new triterpene derivatives of azadirachtin having the formulae 2–11 shown in FIGS. 2–4 which comprises:

(a) grinding neem plant to form a powder.

(b) extracting the powder with a binary immiscible solvent consisting of a polar and a non-polar solvent in a ratio of 1:2 to obtain an extract;

(c) filtering the extract to obtain a filtrate having two layers, one layer containing lipids and the second layer comprising new triterpene derivatives of azadirachtin, known derivatives of azadirachting, azadirachtin and water soluble constituents;

(d) separating the layers;

(e) concentrating the layer comprising the new triterpene derivatives of azadirachtin, known derivatives of azadirchtin, azadirachtin and water soluble constituents;

(f) treating the concentrate of step (e) with a polar solvent;

(g) filtering the solution of step (f) to produce a filtrate containing a mixture of the new triterpene derivatives of azadirachtin, known derivatives of azadirachtin, and azadirachtin; and (h) separating the new triterpene derivatives of azadirachtin of the formulae 2–11 chromatographically.

2. A process for preparing an insecticidally active composition comprising azadirachtin and triterpene derivatives of azadirachtin from a neem plant which comprises:

(a) grinding dried parts of the neem plant to form a powder;

(b) extracting the powder with a binary immiscible solvent consisting of a polar and a non-polar solvent in a ratio of 1:2 to obtain an extract;

(c) filtering the extract to obtain a filtrate having two layers, one layer containing lipids and the second layer comprising azadirachtin, triterpene derivatives of azadirachtin and water soluble constituents (d) separating the layers;

(e) concentrating the layer containing azadirachtin and triterpene derivatives of azadirachtin and water soluble constituents to form a concentrate;

(f) warming the concentrate of step (e) with a polar solvent to form a solution and (g) filtering the solution of step (f) to produce a filtrate comprising a mixture of azadirachtin and triterpene derivatives of azadirachtin.

3. A process for preparing an insecticidally active composition comprising unsaturated lipids from a neem plant which comprises:

(a) grinding the neem plant to form a powder;

(b) extracting the powder with a mixture of two immiscible solvents consisting of a polar and a non-polar solvent in a ratio of 1:2 to obtain an extract;

(c) filtering the extract to obtain a filtrate having two layers; a first layer containing lipids said lipids comprising saturated and unsaturated lipids and a second layer comprising azadirachtin, triterpene derivatives of azadirachtin and water soluble constituents;

(d) separating the layers;

(e) concentrating the layer containing the lipids to form a concentrate;

(f) dissolving the concentrate of step (e) with a polar solvent and cooling to a temperature in the range 0° to −10° C. and filtering to produce a filtrate containing unsaturated lipids.

4. A process as claimed in claim 1 wherein the part of the neem plant employed is selected from the seed or seed cake.

5. A process as claimed in claim 1 wherein the polar solvent used in step (b) and in step (f) is selected from chloroform, ethanol, methanol, butanol, isobutanol, carbon tetrachloride, ethylacetate ethylenedichloride, or acetone.

6. A process as claimed in claim 1 wherein the non-polar solvent used is selected from hexane, heptane, or pentane.

7. A process as claimed in claim 1 wherein the separation of the layers is effected by partitioning between a polar and a nonpolar solvent immiscible solvents.

8. A process as claimed in claim 2 wherein the part of the plant employed is selected from the seed or seed cake.

9. A process as claimed in claim 3 wherein the part of the plant employed is selected from the seed or seed cake.

10. A process as claimed in claim 2 wherein the polar solvent used in step (b) and in step (f) is selected from chloroform, ethanol, methanol, butanol, isobutanol, ethylenedichloride, carbon tetrachloride, ethylacetate or acetone.

11. A process as claimed in claim 3 wherein the polar solvent used in step (b) and in step (f) is selected from chloroform, ethanol, methanol, butanol, ethylenedichloride or isobutanol.

12. A process as claimed in claim 2 wherein the non-polar solvent used is selected from hexane, heptane, pentane, benzene or toluene.

13. A process as claimed in claim 3 wherein the non-polar solvent used is selected from hexane, heptane, pentane, benzene or toluene.

14. A process as claimed in claim 2 wherein the separation of the layers is effected by partitioning between a polar and a non-polar immiscible solvent.

15. A process as claimed in claim 3 wherein the separation of the layers is effected by partitioning between a polar and a nonpolar immiscible solvent.

* * * * *